United States Patent [19]
Walters et al.

[11] 3,973,167
[45] Aug. 3, 1976

[54] SPARK SOURCES WITH ELECTRONIC SWITCHING TUBES

[75] Inventors: John P. Walters, Madison, Wis.; John A. Bernier, Lexington, Mass.

[73] Assignees: Wisconsin Alumni Research Foundation, Madison, Wis.; Fisher Scientific Company, Pittsburg, Pa.

[22] Filed: Apr. 16, 1975

[21] Appl. No.: 568,577

Related U.S. Application Data

[63] Continuation-in-part of Ser. No. 445,318, Feb. 22, 1975, abandoned.

[52] U.S. Cl. ........................... 315/207; 315/209 R; 315/240; 315/243
[51] Int. Cl.² ........................................... H05B 37/00
[58] Field of Search ......... 315/207, 209 R, 209 CD, 315/227 R, 237, 238, 240, 241 R, 242, 243, 244

[56] References Cited
UNITED STATES PATENTS
3,749,975    7/1973    Walters ........................... 315/241 R Primary Examiner—James B. Mullins
Attorney, Agent, or Firm—Burmeister, York, Palmatier, Hamby & Jones

[57] ABSTRACT

A spark source is disclosed having an analytical spark gap, a capacitor, a power supply for charging the capacitor, and an electronic switching tube connected in a series circuit between the capacitor and the spark gap. When the tube is rendered conductive by a triggering pulse or other signal, the capacitor is discharged through the spark gap and the switching tube, which carries the entire discharge current.

27 Claims, 6 Drawing Figures

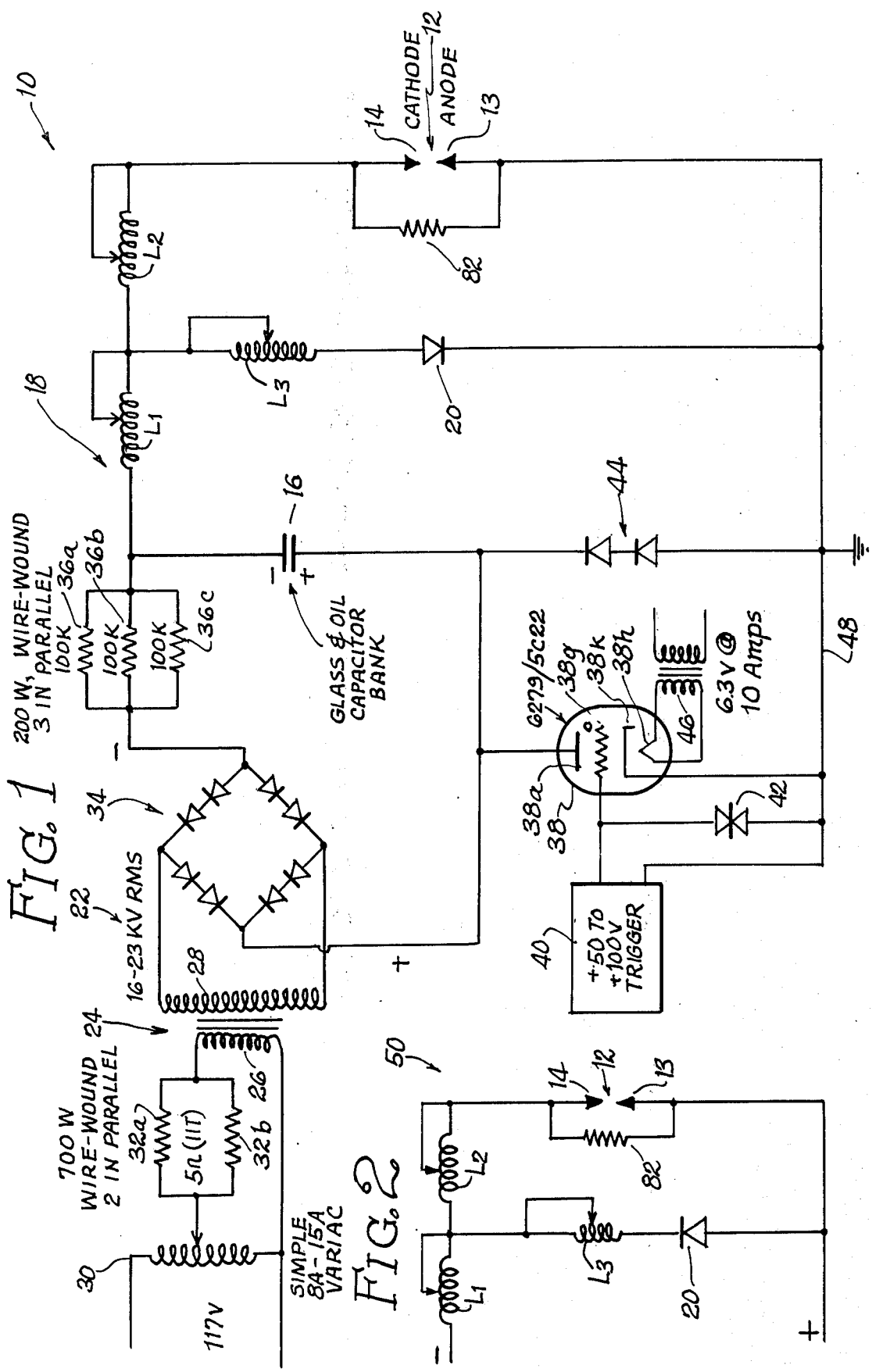

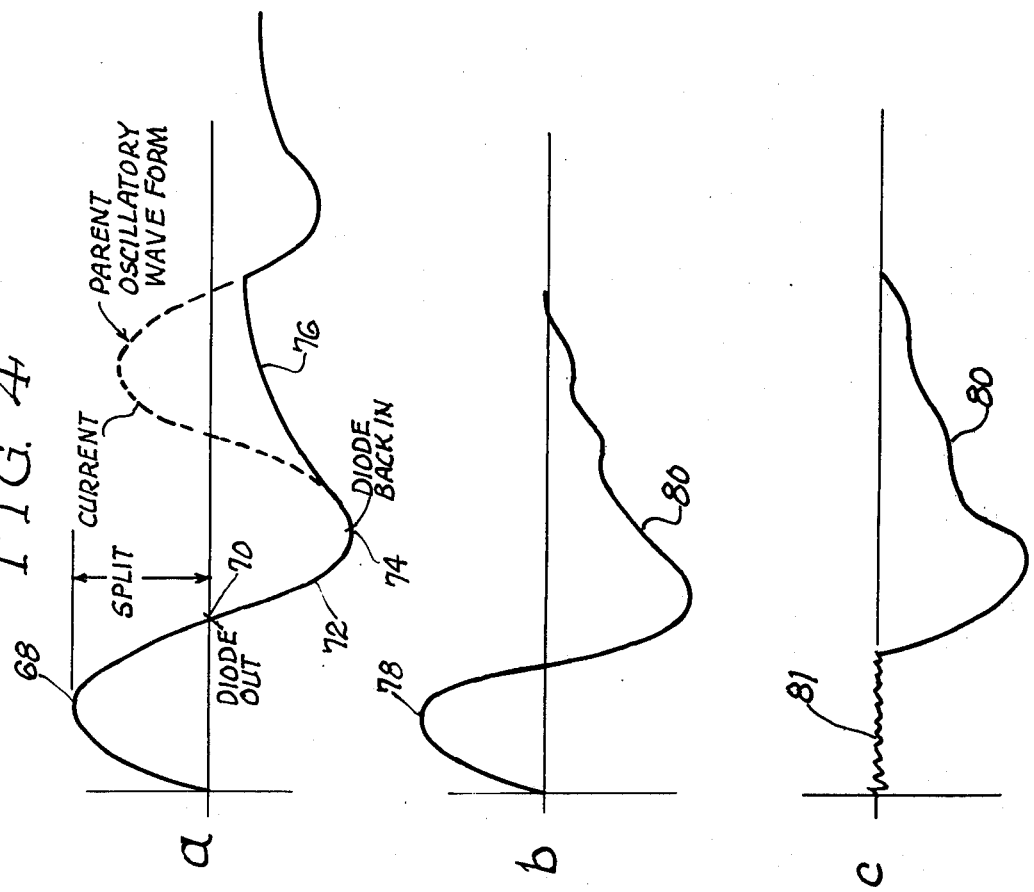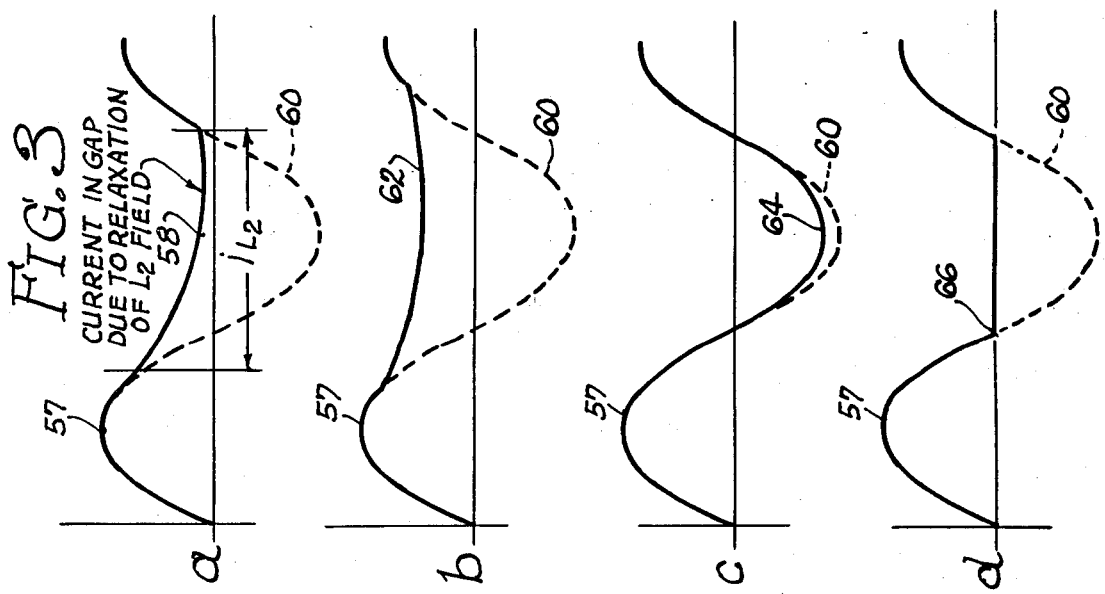

SPARK SOURCES WITH ELECTRONIC SWITCHING TUBES

The United States Government has rights in this invention pursuant to Grant No. NSF-74-76-GP-35602X awarded by the National Science Foundation.

This application is a continuation-in-part of our co-pending application, Ser. No. 445,318, filed Feb. 22, 1975, now abandoned.

This invention relates to spark sources, which may be employed for various purposes, particularly the production of light for spectroscopic analysis. The material to be analyzed is introduced into an analytical spark gap, across which sparks are produced. The sparks vaporize the material to be analyzed and excite the resulting vapor to produce light which can be analyzed spectroscopically to determine the constituents of the material being analyzed.

One object of the present invention is to provide an improved spark source of the general type disclosed and claimed in U.S. Pat. No. 3,749,975, issued July 31, 1973, upon the application of John P. Walters, one of the applicants herein. Such patent discloses a spark source in which a capacitor is charged to a high voltage, and is then discharged across an analytical spark gap. A control gap is also employed in series with the analytical gap. To control the waveform of the discharge current across the analytical spark gap, first and second variable coils or inductive elements are provided in series with the capacitor and the spark gaps. A shunting diode is connected across the series combination of the analytical spark gap and the second inductive element.

In the spark source of such Walters patent, a gaseous electronic control tube is connected in parallel with the control gap. The discharge of the capacitor across the analytical spark gap can be initiated by applying a control pulse or other signal to the control electrode of the electronic control tube, so as to render it conductive, which has the effect of momentarily short-circuiting the control gap. The increased voltage across the analytical gap then causes the initiation of the discharge of the capacitor across the analytical gap. After a very brief interval, the control gap also breaks down, so that it carries the main discharge current between the capacitor and the analytical spark gap.

In accordance with one object of the present invention, the control spark gap is eliminated, and an electronic switching tube is connected directly into the series circuit between the capacitor and the analytical spark gap. The tube may be rendered conductive by supplying a control pulse or other signal to the control electrode of the tube. The increased voltage across the analytical spark gap then causes such gap to break down so that the capacitor is discharged across the gap.

In accordance with another object of the present invention, the circuit of the spark source is arranged so that the cathode of the electronic switching tube is grounded, as is one of the electrodes of the analytical spark gap. With this arrangement, the cathode and the cathode heater of the switching tube are at ground potential, so that the power supply for the heater does not have to be insulated from ground. Moreover, control pulses can readily be supplied between the control electrode and the grounded cathode of the switching tube, without any need to isolate the source of the trigger impulses from the high voltage power supply.

It is advantageous to ground one electrode of the analytical spark gap for reasons of convenience and safety. Moreover, when metal samples or the like are to be analyzed, it is advantageous to mount each sample on the grounded spark gap electrode, so that the sparks will be produced between the sample and the ungrounded electrode. With this arrangement, however, the grounded spark gap electrode becomes the anode during the first half cycle of the oscillatory discharge current. For spectroscopic analysis, it is preferred that the sample be used as the cathode rather than the anode.

To deal with this problem, the present invention employs a shunting diode which is forward biased so that it is conductive during the first half cycle. A third variable coil or inductance element is preferably connected in series with the forward biased shunting diode. By adjusting the third inductance element, in conjunction with the adjustment of the first and second inductance elements, it is possible to produce a uni-directional reversely polarized current across the analytical spark gap, after the initial half cycle. Thus, the grounded sample electrode is the anode during the first half cycle, but becomes the cathode during the remaining portions of the spark discharge.

The third inductive element may also be employed when the shunting diode is polarized so that it is back biased during the first half cycle of the capacitor discharge current. The third inductance element provides additional control over the waveform of the discharge current.

Further objects, advantages and features of the present invention will appear from the following description, taken with the accompanying drawings, in which:

FIG. 1 is a schematic circuit diagram of a spark source to be described as an illustrative embodiment of the present invention.

FIG. 2 is a fragmentary schematic circuit diagram showing a modified spark source in which the shunting diode is reversed in polarity so as to be forward biased rather than back biased during the first half cycle of the capacitor discharge current.

FIG. 3, which contains parts a, b, c and d, is a family of waveform diagrams illustrating the operation of the spark source shown in FIG. 1, with the shunting diode back biased.

FIG. 4, which contains parts a, b and c, is a family of waveform diagrams illustrating the operation of the spark source of FIG. 2, in which the shunting diode is forward biased.

Figure 5:
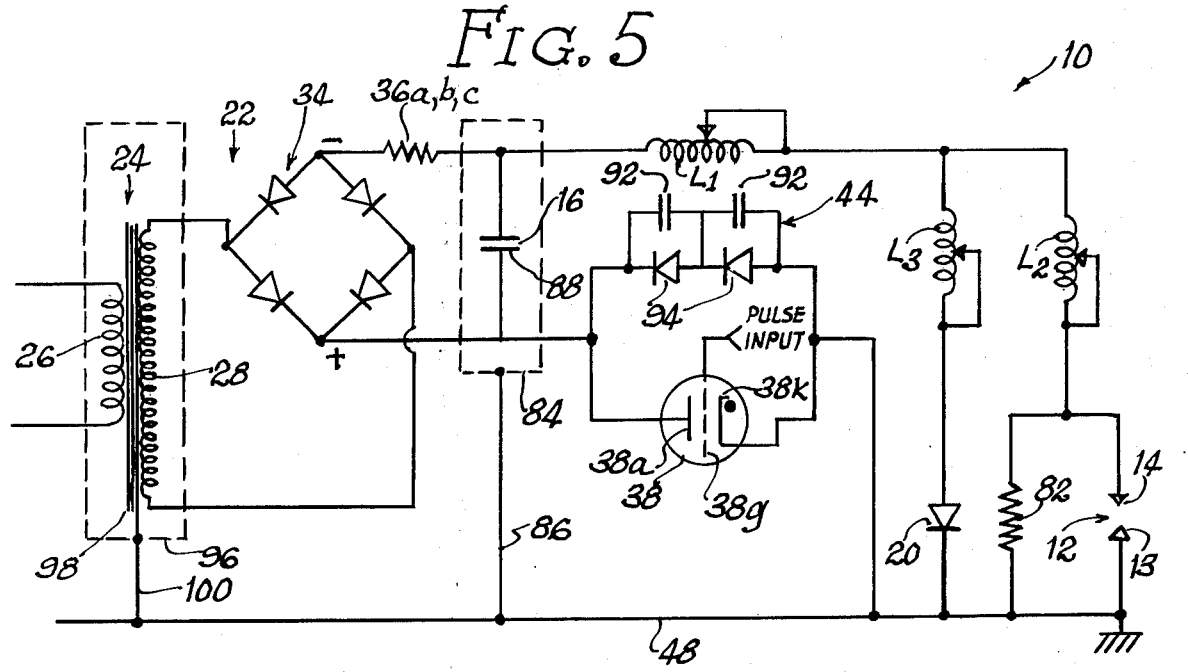
Figure 6:
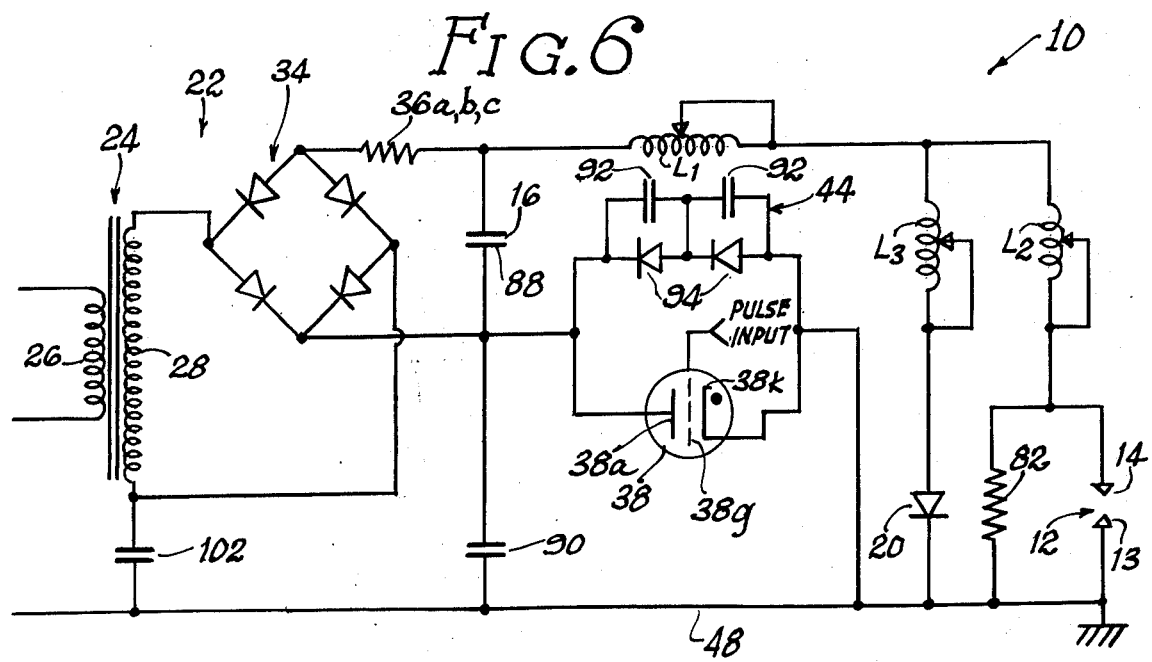

FIGS. 5 and 6 are circuit diagrams similar to FIG. 1, but illustrating the effect of shunting capacitance elements across the electronic switching tube.

As just indicated, FIG. 1 illustrates a spark source 10 which employs an analytical spark gap 12 having electrodes 13 and 14. A spark is produced across the gap 12 by charging a capacitor 16 to a high voltage, and then discharging the capacitor across the gap 12. It is preferred to ground one electrode of the spark gap, in this case the electrode 13.

Thus the spark gap 12 and the capacitor are connected in a series discharge circuit 18 which preferably also includes first and second inductance coils or other inductive elements $L_1$ and $L_2$, connected in series between the capacitor 16 and the spark gap 12. The inductive elements $L_1$ and $L_2$ are preferably variable or adjustable, so that the inductive elements may be employed to control the waveform and the periodically or frequency of the discharge current. It is also preferred to provide a shunting diode 20, in a shunting relationship to the series combination of the spark gap 12 and the second inductive element $L_2$. A third inductance coil or other inductive element $L_3$ is preferably connected in series with the shunting diode 20. Here again, the third inductance element $L_3$ is preferably variable or adjustable, to provide a further control over the wavefrom of the current across the spark gap 12.

A high voltage power supply 22 is provided to charge the capacitor 16. The high voltage power supply 22 may be of any known or suitable construction. As shown, the power supply 22 includes a high voltage transformer 24 having a low voltage primary winding 26 and a high voltage secondary winding 28. A commercial alternating source may be employed to energize the primary winding 26. As shown, the primary winding 26 is energized through a variable autotransformer 30 and a pair of current limiting resistors 32a and 32b, connected in parallel with each other and in series between the autotransformer 30 and the primary winding 26. It will be understood that the variable autotransformer 30 makes it possible to adjust the high voltage output of the power supply 22.

The high alternating voltage from the secondary winding 28 is rectified by a bridge rectifier circuit 34 which delivers its direct current output to the capacitor 16 through current limiting resistors 36a, b and c, connected in parallel with one another, and in series between the negative terminal of the bridge rectifier 34 and one side of the capacitor 16. The other side of the capacitor is connected to the positive output terminal of the bridge rectifier circuit 34. The charging resistors 36a, b and c, regulate the rate at which the capacitor 16 is charged by the high voltage power supply 22.

In accordance with one feature of the present invention, an electronic switching tube 38 is connected in series with the capacitor discharge circuit 18, so that the capacitor 16 can be discharged across the analytical spark gap 12 on command, when the tube 38 is rendered conductive. The switching tube 38 preferably has an anode 38a, a cathode 38k, a cathode heater 38h and a grid or control electrode 38g. The cathode and the anode 38a and 38k are preferably connected directly into the capacitor discharge circuit 18 between the capacitor 16 and the analytical spark gap 12. The anode 38a is connected to the positive terminal of the bridge rectifier circuit 34, and also to the corresponding terminal of the capacitor 16, such capacitor terminal being positively charged by the power supply 22.

The electronic switching tube 38 is preferably of the gaseous type, such as a thyratron, containing an ionizable gas or vapor, so that an arc discharge will be established between the anode and the cathode when the tube becomes conductive.

The electronic switching tube 38 can be rendered conductive on command by applying a positive trigger pulse or other signal between the control electrode 38g and the cathode 38k. Such pulse or signal may be supplied by a trigger source 40 which may supply positive pulses or approximately 50 to 100 volts. The pulses preferably have sharp positive-going timing edges to produce highly precise triggering of the gaseous switching tube 38.

As shown, a selenium surge suppressor 42 is connected between the control electrode 38g and the cathode 38k. Such surge suppressor may be General Electric type number GRS-21-S A11-D11-9H, or the equivalent.

The electronic switching tube 38 is preferably of the type containing hydrogen, but may be of other types containing other gases or vapors, such as argon and mercury vapor. One suitable type is the commercial type number 6279/5C22, containing hydrogen.

The tube 38 conducts current in one direction, between its anode 38a and its cathode 38k. To conduct current in the opposite direction during the oscillatory capacitor discharge current, a diode rectifier 44 is connected between the anode 38a and the cathode 38k. As illustrated, such rectifier 44 takes the form of a diode stack, polarized so as to be back-biased by the initial positive voltage between the anode 38a and the cathode 38k.

The heater 38h of the gaseous switching tube 38 may be energized by a filament transformer 46, which may be connected to a commercial source of alternating current.

The circuit of the spark source 10 is arranged so that the cathode 38k of the gaseous switching tube 38 is connected to ground. Thus, in FIG. 1, the cathode 38k is connected to a grounded lead or conductor 48. With this arrangement, there is no need to provide special high voltage insulation between the primary and secondary windings of the filament transformer 46. Moreover, no high voltage can be developed between the cathode 38k and the heater 38h. In addition, it is easy to supply pulses or triggering signals between the control electrode 38g and the cathode 38k, because no high voltage can be developed on the cathode. Thus, it is not necessary to utilize an isolating transformer or any other device to protect the trigger source 40 from the high voltage.

Due to the grounding of the cathode 38k, the anode 38a of the switching tube 38 is connected directly to the positive terminal of the capacitor 16. Thus, the tube 38 is polarized to carry the initial discharge current between the capacitor 16 and the analytical spark gap 12.

It is also highly desirable to ground one electrode of the analytical spark gap 12, for reasons of safety and convenience. In this case, the electrode 13 is grounded and thus is connected directly to the grounded cathode 38k of the electronic switching tube 38. With this polarization, the grounded electrode 13 becomes the anode during the initial half cycle of the oscillatory discharge current produced between the capacitor 16 and the spark gap 12.

In the operation of the spark source 10 of FIG. 1, the capacitor 16 is charged through the resistors 36a, b and c by the high voltage power supply 22. As long as the gaseous switching tube 38 is non-conductive, no spark is produced. The diode 44 is back-biased and is non-conductive.

A spark discharge can be produced on command by applying a positive triggering pulse or voltage between the control electrode 38g and the cathode 38k of the tube 38, to trigger the tube into conduction. The triggering pulses can be supplied by a computer, some other programmed control system, or any other control device.

When the tube 38 becomes conductive, the high voltage across the capacitor 16 is applied across the analytical spark gap 12 causing it to break down into conduction so that a spark discharge is produced. Due to the presence of both capacitance and inductance in the discharge circuit, the discharge current is oscillatory. The first half cycle of the oscillatory spark discharge current is carried by the tube 38. The reversely polarized current during the second half cycle is carried by the diode rectifier 44. During the remainder of the damped oscillatory discharge, the forwardly polarized current is carried by the conductive tube 38, while the reverse current is carried by the diode rectifier 44, during alternate half cycles.

The provision of the gaseous switching tube 38 makes it possible to produce sparks on command, and to time the sparks with a high degree of precision. With respect to the precise timing of the sparks, the present invention constitutes a significant improvement over the control gap arrangements used heretofore. The precise firing of the gaseous switching tube 38 is not affected by atmospheric variations and other physical factors which do not affect the breakdown of an atmospheric control gap. The ability to time the sparks with greatly improved precision is an important advantage of the present invention.

In addition, the provision of the gaseous switching tube 38 substantially eliminates the loud noises produced by the sparks jumping across the control gap, as used heretofore. The reduction in noise is quite dramatic and is an important environmental advantage of the present invention.

In FIG. 1, the shunting diode 20 is polarized so as to be back-biased during the first half cycle of the capacitor discharge current. The effect of this polarization will be discussed presently.

FIG. 2 illustrates a modified spark source 50, in which the shunting diode 20 is reversed in polarity so as to be forward biased during the initial half cycle of the oscillatory discharge current. Otherwise, the spark source 50 of FIG. 2 may be the same as the spark source 10 of FIG. 1. The significance of reversing the polarization of the shunting diode 20 will be discussed presently.

FIG. 3 illustrates the waveform of the spark current across the analytical spark gap 12 for the spark source 52 of FIG. 1, in which the shunting diode 20 is reverse biased during the first current half cycle of the capacitor discharge, but with the inductance of $L_3$ reduced to zero or omitted so that only the stray inductance of the circuit is in series with the shunting diode 20. Due to the back bias, the diode 20 is non-conductive initially so that the entire current during the first half cycle passes through $L_2$ and across the spark gap 12. The buildup of current in the inductive element $L_2$ results in the storage of energy in $L_2$. The stored energy produces a relaxation current across the spark gap 12 during the second half cycle.

In FIG. 3a, the current across the spark gap during the first half cycle is indicated at 57. The current in the spark gap 12 due to the relaxation of $L_2$ during the second half cycle is indicated at 58. This current flows during the interval indicated as $i_{L2}$, when the shunting diode 20 is forward biased. In FIG. 3a, the broken line 60 represents the current that would flow across the spark gap 12 during the second half cycle in the absence of the relaxation current produced by $L_2$.

The waveform of the current across the spark gap during the interval $i_{L2}$ is completely independent of the main oscillatory capacitor discharge current. Such current waveform, in direction and in mangitude, depends on the value of $L_2$. The effect of changing the magnitude of $L_2$ is illustrated by FIGS. 3a, b and c. If $L_2$ is large, as it is for FIGS. 3a and b, the relaxation current may be high enough to drive the discharge uni-directional. Thus, the uni-directional discharge current across the spark gap is indicated at 58 in FIG. 3a and at 62 in FIG. 3b. It will be evident that FIG. 3b represents a case in which $L_2$ is larger than for the case represented by FIG. 3a, with the result that the relaxation current produced by $L_2$ is greater, as will be evident from a comparison of the currents represented at 62 and 58.

FIG. 3c represents the case in which $L_2$ is relatively small, so that the relaxation current is insufficient to produce a uni-directional discharge current across the spark gap. Instead, the relaxation current reduces the oppositely polarized current during the second half cycle, as indicated at 64, but does not change the polarity of such current. It will be evident that the waveform of the discharge current across the spark gap 12 can be changed to a great extent by changing the value of $L_2$.

The examples illustrated by FIGS. 3a, b and c presuppose that the impedance of the shunting diode 20, when it is forward biased, is high enough to keep the analytical spark gap 12 in conduction during all phases of the discharge. If not, there may not be any relaxation current from $L_2$. Instead, the action of the diode 20 may be simply to clip the discharge current, particularly when $L_2$ is small in value. This clipping action is illustrated in FIG. 3d at 66. At such point 66, the spark gap 12 goes out of conduction, due to the very low impedance of the shunting diode when it is forward biased. The clipping action continues throughout the half cycle, as long as the diode is forward biased. This clipping action depends upon the specific characteristics of the diode which is employed, and upon the residual impedance in series with the diode, due to the resistance and distributed inductances of the connecting leads, for example.

The provision of the third inductance element $L_3$ in series with the shunting diode 20 has the advantage of increasing the impedance of the diode circuit when the diode is forward biased. In this way, the discharge across the spark gap 12 will be maintained during all phases of the capacitor discharge. This situation is represented by the spark source 10 of FIG. 1, in which the third inductive element $L_3$ is connected in series with the shunting diode 20, which is reverse biased during the first half cycle and is forward biased during the second half cycle. The waveforms of the spark currents across the spark gap 12 may be represented by the waveform diagrams of FIGS. 3a, b and c, depending upon the value of the second inductive element $L_2$.

Thus, the inductance $L_3$ acts as a forward-unit impedance, inserted into the diode loop, to control the breakdown and continued ionization of the analytical gap 12. When $L_3$ is adjustable, it may be called a programmed forward-unit impedance.

The action of $L_3$ is to control the splitting of the current between the diode 20 and the gap 12. The inductance $L_3$ will allow the gap 12 to stay in conduction when $L_2$ is small and the diode 20 is forward biased and in full conduction.

In the case of the spark source 10 of FIG. 1, the grounded electrode 13 is the anode during the first half cycle of the oscillatory discharge. If the value of $L_2$ is sufficiently large to produce a uni-directional spark current, as illustrated by FIGS. 3a and b, the grounded electrode 13 is the anode for the entire discharge. This has the disadvantage that it is convenient and otherwise desirable to mount the sample to be analyzed on the grounded electrode, so that the sparks will be produced between the sample and the ungrounded electrode. For the purposes of spectroscopic analysis, it is generally preferable for the sample to be used as the cathode rather than the anode. Of course, this disadvantage can be overcome by mounting the sample on the ungrounded electrode 14.

Another way of dealing with this problem is to reverse the polarity of the shunting diode 20, as illustrated in FIG. 2. With this polarity, the diode 20 is forward biased during the first half cycle and is reverse biased during the second half cycle. As a result of reversing the polarity of the diode in this manner, an entirely new class of discharge waveforms can be generated. These new waveforms constitute a substantial addition to the class of waveforms that are available to practical spectro-chemistry.

As shown in FIG. 2, the third inductive element $L_3$ is connected in series with the shunting diode 20. $L_3$ is preferably variable or adjustable and may range in value from zero to 100 microhenries, for example. The diode is arranged so that it is initially foward biased, during the initial portion of the first current half cycle.

If the inductance $L_3$ is not too small, it increases the impedance in the diode path to such an extent that the spark gap 12 will be broken down into conduction even though the diode 20 is forward biased and is conductive during the initial half cycle. In this case, the current will split between the spark gap and the shunting diode during the first current half cycle, so that both $L_2$ and $L_3$ will be charged with energy.

When the main oscillatory discharge current in the capacitor circuit is reversed in direction, during the second half cycle, the diode 20 is reverse biased, with the result that the diode becomes non-conductive, so that the diode path is opened. The full parent oscillatory capacitor discharge current is then conducted through the air gap 12. During this half cycle, only the second inductance $L_2$ is charged. If $L_2$ is sufficiently large, the remainder of the spark discharge current is uni-directional.

FIG. 4a illustrates the waveforms involved in this sequence of events. The split current in the spark gap during the first half cycle is indicated at 68. At the point 70, the polarity is reversed, so that the diode 20 is rendered non-conductive. It thus is effectively out of the circuit. The passage of the entire reversely polarized capacitor discharge current across the spark gap during the second half cycle is indicated at 72. At approximately the point indicated at 74, the diode 20 again becomes comductive, to carry the relaxation current produced by the second inductance $L_2$. This relaxation current prevents the reversal of the spark gap current, as indicated at 76, so that the spark current is uni-directional during the remainder of the discharge. It will be recognized that the portion 76 of the waveform corresponds to the portion 58 in FIG. 3a, and also to the portion 62 in FIG. 3b, except that the polarity of the spark current is reversed. In FIG. 4a, as in FIGS. 3a and b, the relaxation current produced by the second inductance $L_2$ causes the spark current to be uni-directional during the remainder of the discharge.

Thus, reversing the polarity of the shunting diode 20, as shown in FIG. 2, while providing the third inductance $L_3$ in series with the diode, makes it possible to produce a class of waveforms, as illustrated in FIG. 4a, in which the current is of one polarity during the first half cycle, and is of the opposite polarity during the remainder of the discharge.

This situation is illustrated in FIG. 4b, in which 78 designates the spark current of one polarity produced during the first half cycle, while 80 designates the spark current of the opposite polarity during the remainder of the discharge. Waveforms of this class can be utilized very advantageously, in that the current 78 of one polarity during the first half cycle can be employed to vaporize sample material from the member to be analyzed, mounted on one of the electrodes.

If the inductance $L_3$ is reduced to a residual value, and the diode itself has a sufficiently low forward bias impedance, the spark gap will not go into conduction during the first half cycle of the capacitor discharge current. As a result, the waveform of the spark current, as represented in FIG. 4b, will be modified in the manner shown in FIG. 4c. During the first half cycle, the spark gap current is essentially zero, as indicated at 81. The current that would normally exist in the spark gap during this portion of the discharge is diverted entirely through the diode, which has such a low impedance that the voltage drop across the diode is insufficient to break down the air gap.

The provision of the electronic switching tube makes it possible to control the timing of the analytical sparks with a high degree of precision, to much better advantage than heretofore. Repetitive sparks can readily be produced under the precise control of externally generated pulses or other timing signals, derived from a computer or any other source.

The ability to produce the spark current waveforms illustrated in FIGS. 3 and 4 constitutes another important advantage of the present invention, resulting from the arrangements involving the shunting diode 20 and the inductive elements $L_2$ and $L_3$.

In FIGS. 1 and 2, a shunting or leak resistor 82 is preferably connected across the air gap 12 to discharge the capacitor 16 when the spark source is shut down. For the spark source 50 of FIG. 2, in which the shunting diode 20 is forward-biased, the resistor 82 may have a high value, such as about 1 megohm. For the spark source 10 of FIG. 1, in which the diode 20 is reverse-biased, the resistor 82 should have a lower value, such as about 10,000 to 100,000 ohms, to prevent premature breakdown of the spark gap 12, as will be explained in detail in connection with FIGS. 5 and 6.

Those skilled in the art will understand that the values of the various components of the spark sources may be varied to suit a variety of conditions. However, it may be helpful, by way of example, to give the following set of values which have been found to be suitable, with the understanding that these values are subject to considerable variation:

16 Glass and oil capacitor bank, 0.01 microfarad.
20 Diode stack.
24 Transformer, 110 volts AC to 16–23 kilovolts RMS.
30 Variac, 8–15 ampere.
32a and 32b Resistors, 5 ohms each, 700 watts, wire-wound.
36a, 36b and 36c Resistors, 100 k ohms each, 200 watts, wire-wound.
38 Thyratron Type 6279/5C22.
42 Selenium surge suppressor, G.E. type No. GRS-21-S-A11-D11-9H.

44 Diode stack.
48 Transformer, 110 to 6.3 volts at 10 amps.
82 1 megohm for FIG. 1; 10,000 to 100,000 ohms for FIG. 2.

The provision of the electronic switching tube has the particular advantage of making it possible to eliminate the control gap heretofore used. The loud noise produced by such control gap, when it breaks down, is thereby eliminated, so that a dramatic reduction in noise is achieved. The resulting improvement in the working environment around the spark source is an important advantage of the present invention.

As previously indicated, the ability to control the timing of the sparks with a high degree of precision is another important advantage of the present invention, resulting from the control circuits involving the gaseous switching tube. The triggering characteristics of the gaseous switching tube are highly precise and not appreciably affected by atmospheric conditions or other environmental factors. When a positive triggering pulse or signal of sufficient magnitude is applied to the control electrode of the gaseous switching tube, the tube is rendered conductive so that a spark is produced with minimal delay. Thus, the timing of the spark is precisely controlled.

With the spark source 10 of FIG. 1, in which the shunting diode 20 is reverse biased during the initial half cycle of the oscillatory capacitor discharge current, it has been found that, under certain conditions, there is a tendency for the spark across the gap 12 to be ignited prematurely, before the triggering pulse is supplied to the control tube 38. This premature ignition of the spark does not occur with the spark source 50 of FIG. 2, in which the shunting diode 20 is forward biased during the initial half cycle of the capacitor discharge current. Under certain adverse conditions, the tendency toward premature ignition of the spark in the spark source 10 of FIG. 1 result in erratic operation of the spark source, so that some of the sparks may not be precisely timed by the triggering pulses supplied to the control tube 38.

Such erratic operation tends to occur with the spark source 10 of FIG. 1 when the spark gap 12 is adjusted to a relatively narrow width, so that the spark gap is easily broken down. The value of the shunting resistor 82 across the spark gap 12 is also a factor in determining whether premature ignition of the spark tends to occur. For any particular spark gap width, premature ignition of the spark is more likely to occur when the shunting resistor 82 has a high value. Reducing the value of the shunting resistor 82 has the effect of preventing the premature ignition of the spark. Thus, when the shunting diode 20 is reverse biased, as it is in FIG. 1, it is preferred to assign a relatively low value of resistance, such as, on the order of 10,000 to 100,000 ohms, to the shunting resistor 82, so as to prevent the erratic operation which results from premature ignition of the spark.

Analysis of the spark source 10 of FIG. 1 has shown that the tendency toward premature ignition of the spark is caused by distributed capacitances and other unwanted capacitances which partially bypass the control tube 28 so that a high voltage is applied across the spark gap 12 during the charging of the main capacitor 16, even though the control tube 38 is nonconductive. As the main capacitor 16 is charged, the voltage coupled across the spark gap 12 by these stray capacitances may become sufficient to break down the spark gap so as to cause premature ignition of the spark, before the tube 38 is supplied with a triggering pulse. When the shunting diode 20 is reverse biased, as it is in FIG. 1, the impedance across the spark gap 12 is high so that the voltage coupled across the gap by stray capacitances can rise to a high value, sufficient to break down the spark gap. When the shunting diode 20 is forward biased, as it is in FIG. 2, the impedance across the spark gap 12 is low, due to the shunting action of the diode 20, so that the voltage coupled across the spark gap by stray capacitances cannot rise to a sufficiently high value to break down the spark gap.

The nature and effect of the stray capacitances is illustrated in FIGS. 5 and 6, which illustrate the same spark source 10 as in FIG. 1, but with certain additions related to the stray capacitances. Generally, any capacitance which is effectively connected between the ungrounded anode 38a and the grounded cathode 38k of the control tube 38 tends to couple a voltage across the spark gap 12 during the charging cycle of the main capacitor 16. It will be noted that neither side of the capacitor 16 is grounded and that one side of the capacitor 16 is connected to the anode 38a of the control tube 38.

As illustrated in FIG. 5, the main capacitor 16 generally has a metal case 84 which is connected to ground, usually be being mounted on the metal chassis of the spark source. Thus, a conductive connection 86 is shown between the capacitor case 84 and the ground conductor 48, which may include the metal chassis of the spark source. As previously indicated, the capacitor 16 has one terminal 88 connected to the anode 38a of the control tube 38. The distributed capacitance between this terminal 88, and the grounded case 84 is effectively connected between the anode 38a and ground, as represented symbolically in FIG. 6 by the capacitance element 90 which may also be regarded as including other stray capacitances, such as the interelectrode capacitance between the anode 38a and the cathode 38k, and the distributed capacitance between the anode leads and ground.

The diode stack 44 connected between the anode 38a and the cathode 38k also generally contributes a component of shunting capacitance, which may arise from the interelectrode capacitances of the diodes in the stack, and also from the small voltage dividing capacitors 92 wich are often incorporated into the diode stack 44 to bring about a substantially uniform division of the inverse voltage along the several diodes in the stack. These voltage dividing capacitors 92 are connected across the individual diodes 94 in the stack 44, which usually comprises a multiplicity of such diodes, connected in series. Although only two such diodes 94 are illustrated in FIGS. 5 and 6, it will be understood that the stack 44 may include any desired number of such diodes connected in series to achieve the required inverse voltage rating. It will be evident that the series string of voltage dividing capacitors 92 provides a shunting capacitance between the anode 38a and the grounded cathode 38k.

As shown in FIG. 5, the high voltage transformer 24 generally has a metal housing 96 and a core 98, which is usually made of iron. The housing 96 and the core 98 are usually grounded, as indicated by the ground connection 100. Ordinarily, the housing 96 and the core 98 are grounded by being mounted on the metal chassis of the spark source 10. It will be understood that there is distributed capacitance between the secondary winding 28 of the transformer 24 and the grounded housing 96 and the core 98. This distributed capacitance is represented diagrammatically by a capacitor element 102 in FIG. 6. It will be understood that the distribued capacitance, represented by the capacitor element 102, effectively provides additional shunting capacitance between the anode 38a of the control tube 38 and ground.

During the charging of the main capacitor 16, the shunting capacitance represented by the capacitor elements 90, 92, and 102 is effective to couple a portion of the charging voltage across the spark gap 12. As the charging voltage across the capacitor 16 rises, the voltage across the spark gap 12 also rises. If the impedance across the spark gap 12 is high, and if the width of the spark gap is not too great, the sparak gap 12 may break down prematurely, before the triggering pulse is supplied to the control tube 38. Such premature breakdown is due to the coupling of a portion of the charging voltage across the spark gap 12 by the shunting capacitance between the anode 38a and ground, such shunting capacitance being represented by the capacitor elements 90, 92 and 102 in FIG. 6.

The premature ignition of the spark across the spark gap 12 can readily be prevented by reducing the resistance of the shunting resistor 82, so as to reduce the impedance across the spark gap 12. For example, the value of the resistor 82 may be reduced to about 10,000 to 100,000 ohms, which will ordinarily prevent the premature breakdown of the spark gap 12, for the usual range of spark gap widths. The reduced value of the resistor 82 reduces the portion of the charging voltage which is developed across the spark gap 12 due to the capacitive coupling afforded by the shunting capacitor elements 90, 92 and 102.

Premature ignition of the spark can also be prevented by increasing the width of the spark gap 12. The proper combination of the width of the spark gap and the value of the shunting resistor 82 will prevent premature breakdown of the spark gap in every instance. For any particular spark gap width, the value of the shunting resistor 82 should be reduced until premature breakdown of the spark gap 12 does not occur. The spark will then be under the precise control of the triggering pulses supplied to the control tube 38. The spark gap 12 will not break down until the control tube 38 is rendered conductive by the triggering pulses.

During the charging cycle of the main capacitor 16, the voltage across the capacitor is transmitted to the ungrounded spark gap electrode 14 through the inductance coils $L_1$ and $L_2$. The voltage is coupled to the grounded spark gap electrode 13 through the shunting capacitor elements 90, 92 and 102.

When the shunting diode 20 is forward biased, as it is in FIG. 2, during the charging cycle and the initial portion of the discharge of the capacitor 16, the diode 20 acts as a low impedance which prevents the development of any high voltage across the spark gap 12 during the charging cycle of the capacitor 16. The small shunting capacitances represented by the elements 90, 92 and 102 have an effective impedance which is much higher than that of the shunting diode 20, so that only a very small portion of the charging voltage is coupled across the spark gap 12 by the shunting capacitances.

We claim:

1. A spark source, comprising a spark gap including a grounded electrode and an ungrounded electrode,
a capacitor having positive and negative terminals adapted to be positively and negatively charged,
a power supply for charging said capacitor and having positive and negative terminals,
means connecting said positive and negative terminals of said power supply to said positive and negative terminals of said capacitor,
a discharge circuit connected between said negative terminal of said capacitor and said ungrounded electrode of said spark gap,
an electronic switching tube having an anode, a thermionic cathode and a control electrode,
means connecting said anode to said positive terminal of said capacitor,
means connecting said cathode to said grounded electrode of said spark gap,
a heating circuit for supplying heating power to said thermionic cathode,
and means for supplying control signals between said control electrode and said cathode of said electronic switching tube,
said signals being of such magnitude and polarity as to render said tube conductive so as to cause the discharge of said capacitor across said spark gap,
sparks thereby being produced across said gap in precisely timed relationship to said control signals.

2. A spark source according to claim 1,
in which said discharge circuit includes first and second inductive elements connected in series with said spark gap,
and a shunting diode connected across the series combination of said second inductive element and said spark gap for modifying the waveform of the spark current.

3. A spark source according to claim 2,
in which said shunting diode is reversely polarized relative to the polarization of said electronic switching tube whereby said shunting diode is reverse biased and nonconductive during the first half cycle of the capacitor discharge current.

4. A spark source according to claim 2,
in which said shunting diode is polarized the same as said electronic switching tube and thereby is forward biased and conductive during the first half cycle of the capacitor discharge current.

5. A spark source according to claim 1,
in which said discharge circuit includes first and second inductive elements connected in series with said spark gap,
and a shunting diode circuit connected across the series combination of said second inductive element and said spark gap,
said shunting diode circuit including a shunting diode and a third inductive element connected in series with said shunting diode.

6. A spark source according to claim 5,
in which said shunting diode is polarized the same as said electronic switching tube and thus is forward biased and conductive during the first half cycle of the capacitor discharge current.

7. A spark source according to claim 5,
in which said shunting diode is reversely polarized relative to the polarization of said electronic switching tube and thus is reverse biased and nonconductive during the first half cycle of the capacitor discharge current.

8. A spark source according to claim 5,
in which said shunting diode is polarized the same as said electronic switching tube and thus is forward biased and conductive during the first half cycle of the capacitor discharge current,
said third inductive element being adjustable for controlling the waveform of the spark current across said spark gap.

9. A spark source according to claim 5,
in which said shunting diode is reversely polarized so that said diode is reverse biased and nonconductive during the first half cycle of the capacitor discharge current,
said third inductive element being adjustable for controlling the waveform of the spark current across said spark bap.

10. A spark source according to claim 1,
including diode rectifier means connected between the anode and cathode of said electronic switching tube,
said diode rectifier means being polarized oppositely with respect to the polarization of said electronic switching tube.

11. A spark source according to claim 1,
in which said electronic switching tube is of the gaseous type containing an ionizable gas or vapor.

12. A spark source according to claim 1,
in which said electronic switching tube is of the gaseous type containing hydrogen.

13. A spark source,
comprising a spark gap including first and second electrodes,
a capacitor adapted to be discharged across said spark gap,
power supply means for charging said capacitor,
a charging circuit connected between said power supply means and said capacitor,
and a discharge circuit connecting said spark gap across said capacitor,
said discharge circuit including first and second inductive elements connected in series with said spark gap,
and a shunting diode circuit connected in parallel with the series combination of said spark gap and said second inductive element,
said shunting diode circuit including a shunting diode and a third inductive element in series with said shunting diode,
said power supply means having a predetermined polarity to charge said capacitor with the same polarity,
said shunting diode having a polarization corresponding to the polarization of said power supply means so that said diode is forward biased and conductive during the initial half cycle of the capacitor discharge current,
said first electrode of said spark gap being grounded and being adapted to receive samples to be analyzed,
said power supply means having positive and negative terminals and being polarized such that said positive terminal is connected through portions of said charging and discharging circuits to said grounded first electrode,
said shunting diode and said second and third inductive elements being effective to polarize said grounded electrode as the anode during the first half cycle of the capacitor discharge current while polarizing said grounded electrode as the cathode during the remainder of the capacitor discharge current.

14. A spark source according to claim 13,
in which said third inductive element is adjustable for controlling the waveform of the spark current across said spark gap.

15. A spark source according to claim 14,
in which said second inductive element is adjustable for controlling the waveform of the spark current across said spark gap.

16. A spark source,
comprising a spark gap having a grounded electrode and an ungrounded electrode,
a capacitor adapted to be discharged across said spark gap,
said capacitor having positive and negative terminals adapted to be charged positively and negatively,
a power supply for charging said capacitor,
said power supply having positive and negative terminals connected to said positive and negative terminals of said capacitor,
a discharge circuit connected between said capacitor and said spark gap,
said discharge circuit including means for connecting said positive terminal of said capacitor to said grounded electrode of said spark gap,
said discharge circuit including first and second inductive elements connected in series with said spark gap,
and shunting diode means including a shunting diode and connected across the series combination of said spark gap and said second inductive element,
said shunting diode being polarized the same as the polarization of said capacitor and thereby being forward biased and conductive during the first half cycle of the capacitor discharge current,
whereby said shunting diode splits current away from said spark gap during said first half cycle.

17. A spark source according to claim 16,
in which said second inductive element is adjustable for controlling the waveform of the spark current across said spark gap.

18. A spark source according to claim 16,
in which said second inductive element has sufficient inductance to produce a uni-directional spark current after the first half cycle of the capacitor discharge current,
said uni-directional spark current being polarized oppositely from the capacitor discharge current during the first half cycle.

19. A spark source according to claim 16,
in which said diode has a sufficiently low impedance to prevent the break down of said spark gap during the first half cycle of the capacitor discharge current.

20. A spark source according to claim 19,
in which said second inductive element has sufficient inductance to maintain a uni-directional space current after the initial half cycle of the capacitor discharge current.

21. A spark source,
comprising a spark gap including a grounded electrode and an ungrounded electrode,
a capacitor having positive and negative terminals adapted to be positively and negatively charged,
a power supply for charging said capacitor and having positive and negative terminals, means connecting said positive and negative terminals of said power supply to said positive and negative terminals of said capacitor, a discharge circuit connected between said negative terminal of said capacitor and said ungrounded electrode of said spark gap, an electronic switching tube having an anode, a thermionic cathode and a control electrode, means connecting said anode to said positive terminal of said capacitor, means connecting said cathode to said grounded electrode of said spark gap, a heating circuit for supplying heating power to said thermionic cathode, and means for supplying positive control pulses between said control electrode and said cathode of said electronic switching tube, said pulses being of sufficient magnitude to trigger said tube into a conductive state so as to cause the discharge of said capacitor across said spark gap, sparks thereby being produced across said gap under the precise timing control of said pulses.

22. A spark source, comprising a spark gap including a grounded electrode and an ungrounded electrode, a capacitor having positive and negative terminals adapted to be positively and negatively charged, a power supply for charging said capacitor and having positive and negative terminals, means connecting said positive and negative terminals of said power supply to said positive and negative terminals of said capacitor, a discharge circuit connected between said negative terminal of said capacitor and said ungrounded electrode of said spark gap, an electronic switching tube having an anode, a thermionic cathode and a control electrode, means connecting said anode to said positive terminal of said capacitor, means connecting said cathode to said grounded electrode of said spark gap, a heating circuit for supplying heating power to said thermionic cathode, and means for supplying positive control pulses between said control electrode and said cathode of said electronic switcing tube, said pulses being of sufficient magnitude to trigger said tube into a conductive state so as to cause the discharge of said capacitor across said spark gap, sparks thereby being produced across said gap under the precise timing control of said pulses, and a shunting impedance connected in shunting relationship to said spark gap and of a sufficiently low impedance value to prevent premature breakdown of said spark gap during the charging cycle of said capacitor due to coupling of a portion of charging voltage across said spark gap through distributed capacitance between said positive terminal of said capacitor and ground.

23. A spark source according to claim 22, in which said shunting impedance is in the form of resistance means.

24. A spark source according to claim 23, in which said resistance means has a resistance value on the order of 10,000 to 100,000 ohms.

25. A spark source, comprising a spark gap including a grounded electrode and an ungrounded electrode, a capacitor having positive and negative terminals adapted to be positively and negatively charged, a power supply for charging said capacitor and having positive and negative terminals, means connecting said positive and negative terminals of said power supply to said positive and negative terminals of said capacitor, a discharge circuit connected between said negative terminal of said capacitor and said ungrounded electrode of said spark gap, an electronic switching tube having an anode, a thermionic cathode and a control electrode, means connecting said anode to said positive terminal of said capacitor, means connecting said cathode to said grounded electrode of said spark gap, a heating circuit for supplying heating power to said thermionic cathode, means for supplying positive control pulses between said control electrode and said cathode of said electronic switching tube, said pulses being of sufficient magnitude to trigger said tube into a conductive state so as to cause the discharge of said capacitor across said spark gap, sparks thereby being produced across said gap under the precise timing control of said pulses, a shunting diode connected in shunting relation to said spark gap, said shunting diode having a polarization which is opposite to that of said capacitor so that said shunting diode is back biased and nonconductive during the charging cycle of said capacitor, and a shunting impedance connected in shunting relation to said spark gap and having a sufficiently low impedance to prevent premature breakdown of said spark gap during the charging cycle of said capacitor due to the portion of the charging voltage which is coupled across said spark gap through the distributed capacitance between said positive terminal of said capacitor and said grounded electrode of said spark gap.

26. A spark source according to claim 25, in which said shunting impedance is in the form of resistor means.

27. A spark source according to claim 26, in which said resistor means has a resistance on the order of 10,000 to 100,000 ohms.

* * * * *

PO-1050
(5/69)

UNITED STATES PATENT OFFICE
CERTIFICATE OF CORRECTION

Patent No. 3,973,167     Dated August 3, 1976

Inventor(s) John P. Walters et al

It is certified that error appears in the above-identified patent and that said Letters Patent are hereby corrected as shown below:

Column 2, last line, "periodically" should be "periodicity".

Column 3, line 9, "wavefrom" should be "waveform".

Column 5, line 66, "mangitude" should be "magnitude".

Column 9, line 38, after "FIG. 1" insert "may".

Column 9, line 63, "28" should be "38".

Column 11, line 59, delete the period after "voltage".

Column 13, line 10, after "polarized" insert "relative to the polarization of said electronic switching tube".

Column 13, line 16, "bap" should be "gap".

Column 14, line 59, "space" should be "spark".

Signed and Sealed this

Nineteenth Day of October 1976

[SEAL]

Attest:

RUTH C. MASON
Attesting Officer

C. MARSHALL DANN
Commissioner of Patents and Trademarks